US012661331B2

(12) United States Patent
Planz

(10) Patent No.: US 12,661,331 B2
(45) Date of Patent: Jun. 23, 2026

(54) MEK INHIBITORS FOR THE TREATMENT OF HANTAVIRUS INFECTIONS

(71) Applicant: Atriva Therapeutics GmbH, Tuebingen (DE)

(72) Inventor: Oliver Planz, Dettingen an der Erms (DE)

(73) Assignee: Atriva Therapeutics GmbH, Tuebingen (DE)

( * ) Notice: Subject to any disclaimer, the term of this patent is extended or adjusted under 35 U.S.C. 154(b) by 923 days.

(21) Appl. No.: 17/767,186

(22) PCT Filed: Oct. 7, 2020

(86) PCT No.: PCT/EP2020/078104

§ 371 (c)(1),
(2) Date: Apr. 7, 2022

(87) PCT Pub. No.: WO2021/069486

PCT Pub. Date: Apr. 15, 2021

(65) Prior Publication Data

US 2022/0378730 A1 Dec. 1, 2022

(30) Foreign Application Priority Data

Oct. 8, 2019 (LU) .......................................... 101430
Oct. 16, 2019 (EP) ...................................... 19203601

(51) Int. Cl.

| | |
|---|---|
| ***A61K 31/196*** | (2006.01) |
| ***A61K 31/166*** | (2006.01) |
| ***A61K 31/18*** | (2006.01) |
| ***A61K 31/352*** | (2006.01) |
| ***A61K 31/4184*** | (2006.01) |
| ***A61K 31/437*** | (2006.01) |
| ***A61K 31/44*** | (2006.01) |
| ***A61K 31/4412*** | (2006.01) |
| ***A61K 31/4523*** | (2006.01) |
| ***A61K 31/506*** | (2006.01) |
| ***A61K 31/519*** | (2006.01) |
| ***A61K 31/535*** | (2006.01) |
| ***A61P 31/14*** | (2006.01) |

(52) U.S. Cl.

CPC .......... *A61K 31/196* (2013.01); *A61K 31/166* (2013.01); *A61K 31/18* (2013.01); *A61K 31/352* (2013.01); *A61K 31/4184* (2013.01); *A61K 31/437* (2013.01); *A61K 31/44* (2013.01); *A61K 31/4412* (2013.01); *A61K 31/4523* (2013.01); *A61K 31/506* (2013.01); *A61K 31/519* (2013.01); *A61K 31/535* (2013.01); *A61P 31/14* (2018.01)

(58) Field of Classification Search

CPC ........................................................ A61P 31/14
See application file for complete search history.

(56) References Cited

U.S. PATENT DOCUMENTS

2003/0060469 A1 3/2003 Ludwig et al.

FOREIGN PATENT DOCUMENTS

| | | | |
|---|---|---|---|
| DE | 102014111892 | A1 | 2/2016 |
| WO | 2014/056894 | A1 | 4/2014 |
| WO | 2015/173788 | A1 | 11/2015 |
| WO | 2019/076947 | A1 | 4/2019 |

OTHER PUBLICATIONS

Benn et al., "Hepatitis B Virus HBx Protein Induces Transcription Factor AP-1 by Activation of Extracellular Signal-Regulated and c-Jun N-Terminal Mitogen-Activated Protein Kinases," Journal of Virology, vol. 70, No. 8, Aug. 1996, pp. 4978-4985.
Bruder et al., "Adenovirus Infection Stimulates the Raf/MAPK Signaling Pathway and Induces Interleukin-8 Expression," Journal of Virology, vol. 71, No. 1, Jan. 1997, pp. 398-404.
Chou et al., "Quantitative Analysis of Dose-Effect Relationships: The Combined Effects of Multiple Drugs or Enzyme Inhibitors," Advances in Enzyme Regulation, vol. 22, No. C, Jan. 1984, pp. 27-55.
Chou, T., "Drug Combination Studies and Their Synergy Quantification Using the Chou-Talalay Method," Cancer Research, vol. 70, No. 2, Jan. 2010, pp. 440-446.
Chou, T., "Theoretical Basis, Experimental Design, and Computerized Simulation of Synergism and Antagonism in Drug Combination Studies," Pharmacological Reviews, vol. 58, No. 3, Sep. 2006, pp. 621-681.
Cohen, P., "The search for physiological substrates of MAP and SAP kinases in mammalian cells," Trends in Cell Biology, vol. 7, No. 9, Sep. 1997, pp. 353-361.
Di Veroli et al., "Combenefit: an interactive platform for the analysis and visualization of drug combinations," Bioinformatics, vol. 32, No. 18, Apr. 2016, pp. 2866-2868.
Fischel et al., "Synergistic cytotoxic interaction in hormone-refractory prostate cancer with the triple combination docetaxel-erlotinib and 5-fluoro-5'-deoxyuridine," Anti-Cancer Drugs, vol. 17, No. 7, Aug. 2006, pp. 807-813.
Foucquier et al., "Analysis of drug combinations: current methodological landscape," Pharmacology Research & Perspectives, vol. 3, No. 3, May 2015, p. e00149, 11 pp.
Frémin et al., "From basic research to clinical development of MEK1/2 inhibitors for cancer therapy," Journal of Hematology & Oncology, vol. 3, No. 8, Feb. 2010, pp. 11.
Gantlett et al., "Synergistic inhibition of HIV-1 infection by combinations of soluble polyanions with other potential microbicides," Antiviral Research, vol. 75, No. 3, Mar. 2007, pp. 188-197.
Gubareva et al., "Evidence for Zanamivir Resistance in an Immunocompromised Child Infected with Influenza B Virus," The Journal of Infectious Diseases, vol. 178, No. 5, Nov. 1998, pp. 1257-1262.
Haasbach et al., "The MEK-inhibitor CI-1040 displays broad anti-influenza virus activity in vitro and provides a prolonged treatment window compared to standard of care in vivo," Antiviral Research, vol. 142, Apr. 2017, pp. 178-184.

(Continued)

*Primary Examiner* — James D. Anderson
(74) *Attorney, Agent, or Firm* — Michael A. Whittaker

(57) ABSTRACT

The present invention relates to MEK inhibitors that are capable of displaying one or more beneficial therapeutic effects. The MEK inhibitors can be used in the prevention and/or treatment of hantavirus infection.

14 Claims, 4 Drawing Sheets

(56) References Cited

OTHER PUBLICATIONS

Heyman et al., "Hantavirus infections in Europe: from virus carriers to a major public-health problem," Expert Reviews of Anti-Infective Therapy, vol. 7, No. 2, Mar. 2009, pp. 205-217.
Lin et al., "Compounds from Wedelia chinensis synergistically suppress androgen activity and growth in prostate cancer cells," Carcinogenesis, vol. 28, No. 12, Oct. 2007, pp. 2521-2529.
Ludwig, S., "Targeting cell signalling pathways to fight the flu: towards a paradigm change in anti-influenza therapy," Journal of Antimicrobial Chemotherapy, vol. 64, No. 1, May 2009, pp. 1-4.
Matrosovich et al., "New low-viscosity overlay medium for viral plaque assays," Virology Journal, vol. 3, No. 63, Aug. 2006, pp. 7.
Martinez et al., "Person-to-Person Transmission of Andes Virus," Emerging Infectious Diseases, vol. 11, No. 12, Dec. 2005; pp. 1848-1853.
Popik et al., "Early Activation of Mitogen-Activated Protein Kinase Kinase, Extracellular Signal-Regulated Kinase, p38 Mitogen-Activated Protein Kinase, and c-JunN-Terminal Kinase in Response to Binding of Simian Immunodeficiency Virus to Jurkat T Cells Expressing CCR5 Receptor," Virology, vol. 252, No. 1, Dec. 1998, pp. 210-217.
Robinson et al., "Mitogen-activated protein kinase pathways," Current Opinion in Cell Biology, vol. 9, No. 2, Apr. 1997, pp. 180-186.
Rodems et al., "Extracellular Signal-Regulated Kinase Activity Is Sustained Early during Human Cytomegalovirus Infection," Journal of Virology, vol. 72, No. 11, Nov. 1998, pp. 9173-9180.
Scholtissek et al., "Failure to obtain drug-resistant variants of influenza virus after treatment with inhibiting doses of 3-deazaaadenosine and H7," Archives of Virology, vol. 119, Nos. Mar. 1-2, 1991, pp. 111-118.
Treisman, R., "Regulation of transcription by MAP kinase cascades," Current Opinion in Cell Biology, vol. 8, No. 2, Apr. 1996, pp. 205-215.
Vapalahti et al., "Hantavirus infections in Europe," Lancet Infectious Diseases, vol. 3, No. 10, Oct. 2003, pp. 653-661.
Wyles et al., "Synergy of a Hepatitis C Virus (HCV) NS4A Antagonist in Combination with HCV Protease and Polymerase Inhibitors," Antimicrobial Agents and Chemotherapy, No. 52, No. 5, May 2008, pp. 1862-1864.
Zhao et al., "Evaluation of Combination Chemotherapy: Integration of Nonlinear Regression, Curve Shift, Isobologram, and Combination Index Analyses," Clinical Cancer Research, vol. 10, No. 23, Dec. 2004, pp. 7994-8004.
Groen et al., "A macaque model for hantavirus infection", J Infect Dis. Jul. 1995;172(1):38-44. doi: 10.1093/infdis/172.1.38.
Liu et al., "Vaccines and Therapeutics Against Hantaviruses", Front Microbiol. Jan. 30, 2020:10:2989. doi: 10.3389/fmicb.2019.02989. eCollection 2019.
Ruiz et al., "Animal Models for the Study of Human Disease", Jun. 23, 2017:853-901. doi: 10.1016/978-0-12-809468-6.00033-4.
"Designation for Zapnometinib to treat Hantavirus Infections ", Orphan Drug Designation (ODD) by the U.S. Food and Drug Administration (FDA) for ATR-002 (PD-0184264) the treatment of hantavirus infectionsRetrieved from https://www.atriva-therapeutics.com/2022/01/10/atriva-therapeutics-re . . . on Mar. 21, 2022.
Screenshot of Seach Orphan Drug Designations and Approvals, U.S. Food and Drug Administration (FDA) for zapnometinib 2021.
Preliminary Rejection issued in Korean Patent Application No. 10-2022-7013461 on Nov. 20, 2025.

MEK INHIBITORS FOR THE TREATMENT OF HANTAVIRUS INFECTIONS

PRIORITY CLAIM

This application claims priority to International Application No. PCT/EP2020/078104, filed Oct. 7, 2020, which claims priority to Luxembourg Application No. 101430, filed Oct. 8, 2019 and European Application No. 19203601.0, filed Oct. 16, 2019, wherein the contents of said applications are incorporated herein by reference in their entireties.

BACKGROUND OF THE INVENTION

Hantaviruses (or orthohantavirus) are single-stranded, enveloped, negative-sense RNA viruses in the family Hantaviridae of the order Bunyavirales. To date, 28 pathogenic hantavirus species are known. The hantavirus species differ dependent on their geographic location. In Europe, the prevalent Hantavirus is the Puumala virus, while in the Americas, the Andes virus and the Sin Nombre virus are prevalent. In Asia, the Seoul virus and the Hantaan virus are found. Natural hosts of the hantavirus are rodents, shrews and bats, however, no clinical symptoms are found in natural hosts. Transmission of hantavirus species occurs mainly by aerosolized rodent excreta (urine, saliva, feces), however, in 2005 and 2019, human-to-human transmission of the Andes virus was reported in South America (Martinez VP, Bellomo C, San Juan J, Pinna D, Forlenza R, Elder M, Padula PJ (2005). "Person-to-person transmission of Andes virus". Emerging Infectious Diseases; 11 (12): 1848-1853). For hantavirus species, incubation time in humans last up to several weeks.

Hantavirus infections present a global threat as these infections are associated with a high mortality rate and very limited treatment is available. In humans, hantavirus infections present themselves in two clinical pictures. The first is Hantavirus Hemorrhagic Fever with Renal Syndrome (HFRS), where the mortality rate is 12% and the second is Hantavirus Pulmonary Syndrome (HPS) where the mortality rate is 40%. The severity of the disease depends on the causative hantavirus species and viral load. For example, severe courses of the disease are known to be caused by Hantaan virus, Dobrava-Belgrad virus, Sin Nombre virus and the Andes Virus while more moderate courses of the disease are more likely for example in the Puumala virus or the Saaremaa virus. At least 100.000 HFRS cases are documented per year. In 2004, 40.000-60.000 cases were documented in China alone per year (Zhang et al. 2004, Lee et al. 1996, Lee et al. 1998) compared to about 9.000 in Europe (Vapalahti et al. 2003, Heyman et al. 2009, Heyman et al. 2011).

Currently no FDA or WHO approved vaccines or antivirals are available for the treatment or prevention of hantavirus infections. A vaccine known as Hantavax has been under study since 1990 and is used in Korea, but is not yet generally approved and has limited efficacy. A killed-virus vaccine is not being pursued because of the dangers associated with mass production under high containment as well as the unresolved questions about the efficiency of the vaccine. A number of labs have been working towards a vaccine that would deliver viral antigens by either DNA vectors or as recombinant proteins, but so far none of these vaccines has been shown to be effective.

In addition there is no approved treatment for HPS or HFRS other than alleviation of the symptoms of the diseases. The only drug possibly employed is Ribavirin, but its effectiveness remains unknown. One problem of controlling in particular RNA viruses, such as hantaviruses, is the adaptability of the viruses caused by a high fault rate of the viral polymerases, which makes the production of suitable vaccines as well as the development of antiviral substances very difficult. Most known antiviral medications therefore have been known to lead to resistance in the individual RNA virus species.

Because of the very small genome and thus limited coding capacity for functions being necessary for the replication, all viruses are dependent to a high degree on functions of their host cells. By exertion of influence on such cellular functions necessary for viral replication, it is possible to negatively affect the virus replication in the infected cell. In this scenario, there is no possibility for the virus to replace the lacking cellular function by adaptation, in particular by mutations, in order to thus escape from the selection pressure. This could already be shown for the influenza A virus with relatively unspecific inhibitors against cellular kinases and methyl transferases (Scholtissek and Müller, Arch Virol 119, 111-118, 1991).

It is known in the art that cells have a multitude of signal transmission paths, by means of which signals acting on the cells are transmitted into the cell nucleus. Thereby the cell is capable to react to external stimuli and to react by cell proliferation, cell activation, differentiation, or controlled cell death. It is common to these signal transmission paths that they contain at least one kinase activating by phosphorylation at least one protein subsequently transmitting a signal. When observing the cellular processes induced after virus infections, it is found that a multitude of DNA and RNA viruses preferably activate in the infected host cell a defined signal transmission path, the so-called Raf/MEK/ERK kinase signal transmission path (Benn et al., J Virol 70, 4978-4985, 1996; Bruder and Kovesdi, J Virol 71, 398-404, 1997; Popik and Pitha, Virology 252, 210-217, 1998; Rodems and Spector, J Virol 72, 9173-9180, 1998). This signal transmission path is one of the most important signal transmission paths in a cell and plays a significant role in proliferation and differentiation processes. Growth factor-induced signals are transmitted by successive phosphorylation from the serine/threonine kinase Raf to the dual-specific kinase MEK (MAP kinase kinase/ERK kinase) and finally to the kinase ERK (extracellular signal regulated kinase). Whereas as a kinase substrate for Raf, only MEK is known, and the ERK isoforms were identified as the only substrates for MEK, ERK is able to phosphorylate a whole number of substrates. To these belong for instance transcription factors, whereby the cellular gene expression is directly influenced (Cohen, Trends in Cell Biol 7, 353-361, 1997; Robinson and Cobb, Curr. Opin. Cell Biol 9, 180-186, 1997; Treisman, Curr. Opin. Cell Biol 8, 205-215, 1996).

In view of the prior art, it is clear that there is the need of further compounds and compositions effective in the prevention and treatment of virus diseases in particular in diseases caused by hantavirus species.

In this regard, ongoing research on the usefulness of MEK inhibitors in the treatment of other viral diseases, in particular influenza, has revealed that this class of compounds avoids the disadvantages of the standard antiviral treatments as it is directed to cellular components of the host cells rather than towards the virus itself. For this reason, no resistance to MEK inhibitors has been observed. WO 2001/076570 provides for the concept of treating or preventing infections caused by (−)RNA viruses, in particular by influenza viruses by way of MEK inhibitors. WO 2014/056894 provides for specific MEK inhibitors, such as AZD-6244, AZD-8330, RDEA-119, GSK-1120212 (Trametinib), GDC-0973 (Cobimetinib), CI-1040, PD-0325901, RO-5126766, MSC1936369 (AS-703026) for use in the treatment or prevention of influenza virus infections. In WO 2015/173788 A1 MEK inhibitors are disclosed for use in a method of treating influenza virus and bacterial co-infections. In addition, WO 2019/076947 discloses a new MEK inhibitor, PD-0184264 (also known as ATR-002) for use in a method for the prophylaxis and/or treatment of an influenza viral infection.

However, none of these documents shows that MEK inhibitors could be used for hantavirus infections, and there remains a strong need for the provision of compositions and compounds for the treatment and prevention of hantavirus infections.

SUMMARY OF THE INVENTION

In the present invention, it was found that the use of a MEK inhibitor in the treatment or prevention of a hantavirus infection led to effective treatment of the viral infection. Specifically, a strong reduction of viral load was seen when the MEK inhibitor CI-1040 or PD-0184264 was administered to mice infected with hantavirus.

Thus the present invention relates to a MEK inhibitor for the use in the treatment or prevention of a hantavirus infection in a mammal, preferably a human or a rodent.

In the context of the invention, the MEK inhibitor can be selected from the group consisting of CI-1040, PD-0184264, GSK-1120212, GDC-0973, PLX-4032, AZD6244, AZD8330, AS-703026, RDEA-119, RO-5126766, RO-4987655, PD-0325901, TAK-733, AS703026, PD98059 and PD184352 or pharmaceutically acceptable salt or metabolite thereof. In a preferred aspect, the MEK inhibitor is CI-1040 or PD-0184264.

In human patients, the MEK inhibitor can be administered for the treatment of a hantavirus infection, when the patient shows symptoms of Hantavirus Hemorrhagic Fever with Renal Syndrome (HFRS), or Hantavirus Pulmonary Syndrome (HPS). In these cases, the MEK inhibitor can be administered up to 12 hours, up to 24 hours, up to 48 hours, up to 72 hours or between 4 and 10 days after the first symptoms of HFRS or HPS are observed.

The MEK inhibitor may also be administered for prevention of a hantavirus infection to human subjects who have been in contact with rodents or rodent excrements or are in a region where a hantavirus outbreak is common.

The administration of a MEK inhibitor for the treatment or prevention of a hantavirus infection is particularly indicated when the human subject has been living or visiting in a region known to have hantavirus infections that result in HFRS or HPS.

Such a hantavirus infection can be a Hantaan or a Dobrava virus infection or a hantavirus infection caused by American species such as Black Creek Canal virus (BCCV), New York orthohantavirus (NYV), Monongahela virus (MGLV), Sin Nombre orthohantavirus (SNV), or Andes virus.

The MEK inhibitor for the use of the invention can be preferably administered orally or via inhalation.

In a further aspect, treatment of a rodent population with a MEK inhibitor is contemplated to prevent infection of humans in contact with the rodents. In such uses, the MEK inhibitor could be administered by inhalation, for example via an environmental spray.

FIGURES

Figure 3:
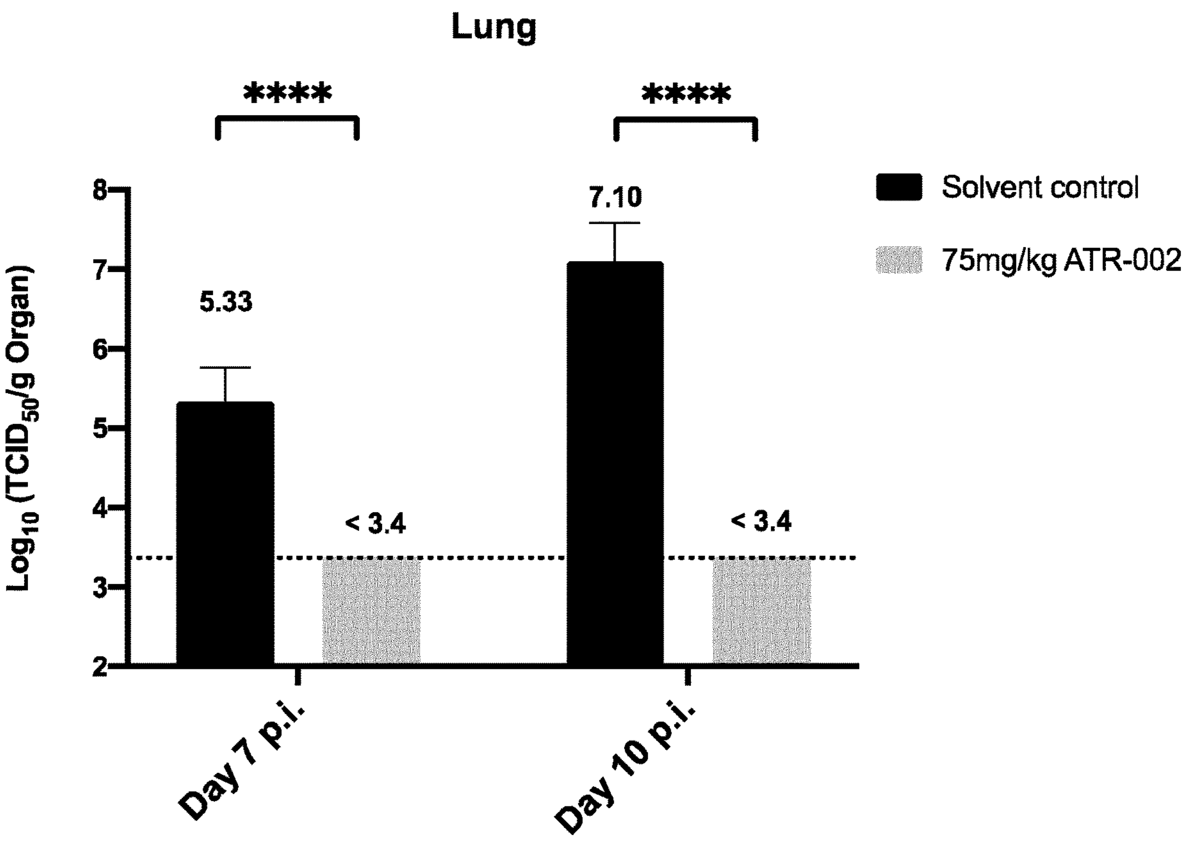

FIG. 3 shows that in the lung of the animals treated with 75 mg/kg/Day ATR-002 no virus could be detected at day 7 and 10 post infection.

Figure 4:
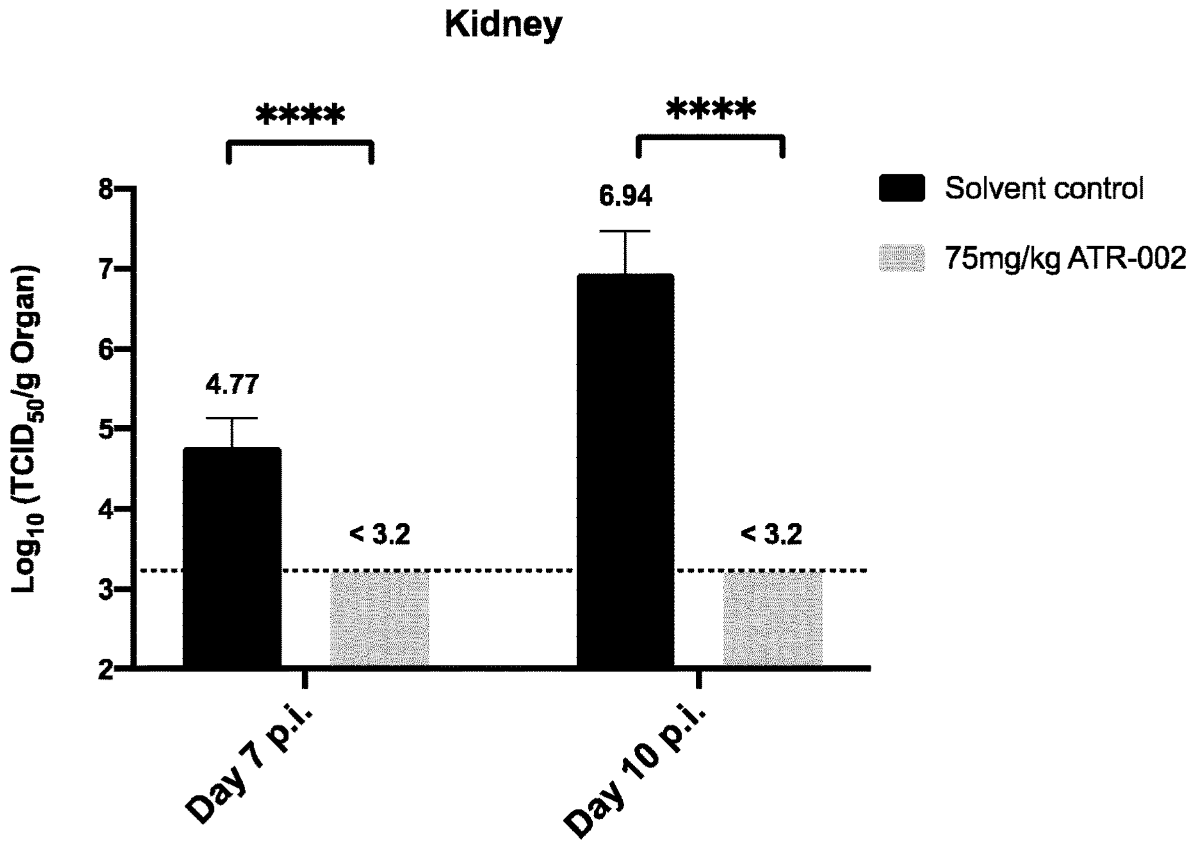

FIG. 4 shows that in the kidney of the animals treated with 75 mg/kg/Day ATR-002 no virus could be detected at day 7 and 10 post infection

DETAILED DESCRIPTION

The following description includes information that may be useful in understanding the present invention. It is not an admission that any of the information provided herein is prior art or relevant to the presently claimed inventions, or that any publication specifically or implicitly referenced is prior art.

"MEK inhibitors" as used herein inhibit the mitogenic signaling cascade Raf/MEK/ERK in cells or in a subject by inhibiting the MEK (mitogen-activated protein kinase kinase). This signaling cascade is hijacked by many viruses, in particular influenza viruses, to boost viral replication. Specific blockade of the Raf/MEK/ERK pathway at the bottleneck MEK therefore impairs growth of viruses, in particular influenza viruses. Additionally, MEK inhibitors show low toxicity and little adverse side effects in humans. There is also no tendency to induce viral resistance (Ludwig, 2009). A particularly preferred MEK inhibitor is PD-0184264 also known as ATR-002.

The MEK inhibitors preferably are selected from CI-1040, PD-0184264 GSK-1120212, GDC-0973, PLX-4032, AZD6244, AZD8330, AS-703026, RDEA-119, RO-5126766, RO-4987655, PD-0325901, TAK-733, AS703026, PD98059 and PD184352 or a pharmaceutically acceptable salt or a metabolite thereof. These MEK inhibitors are known in the art and, for example, described in Table 1 of Fremin and Meloche (2010), J. Hematol. Oncol. 11; 3:8. In the following, structural formulae of PD-0184264 and CI-1040 are shown for reference:

Structural Formula of PD-0184264

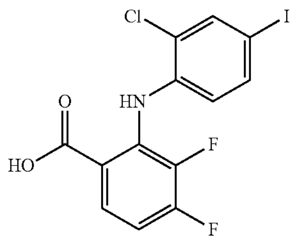

-continued

Structural formula of CI-1040

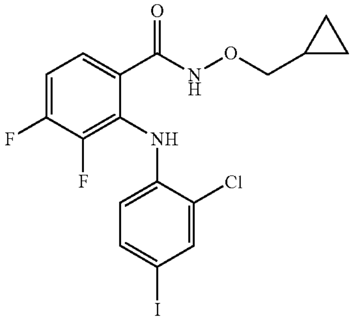

2-(2-chloro-4-iodophenylamino)-N-(cyclopropylmethoxy)-3,4-difluorobenzamide

A "metabolite" as used herein relates to an intermediate end product of metabolism of the MEK inhibitor, which arise during the degradation of the MEK inhibitor by the subject, e.g. in the liver. In a preferred embodiment, the MEK inhibitor is a metabolite of CI-1040, e.g., PD-0184264 is a metabolite of the MEK inhibitor CI-1040.

For the purpose of the invention the MEK inhibitor as defined above also includes the pharmaceutically acceptable salt(s) thereof. The phrase "pharmaceutically or cosmetically acceptable salt(s)", as used herein, means those salts of compounds of the invention that are safe and effective for the desired administration form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, etc.

As already outlined above, hantavirus infections are a public health concern worldwide. Currently, there are no WHO or FDA approved vaccines or antiviral drugs that target hantaviruses. However, in the context of influenza treatment, the inventors demonstrated earlier the antiviral potential of MEK inhibitors, such as CI-140 and PD0184264 (ATR002), the active metabolite of CI-1040 against influenza viruses over in vitro and in vivo levels. From the results presented below, it was shown in in vitro experiments that the propagation of hantaviruses could be successfully reduced in Vero cells treated with 40 μM CI-1040 or 40 μM ATR-002. In example 1, a virus titer reduction of >90% compared to solvent control was observed, see FIGS. 1 and 2. Additionally, in vivo experiments demonstrated that treatment of mice with 75 mg/Kg/Day of ATR-002 over a period of 5 days led to a complete virus titer reduction, compared to animals treated with solvent only, as described in example 2 and FIGS. 3 and 4.

Although hantaviruses replicate in the cytoplasm and are not known to have a nuclear phase, the propagation of PUUV was successfully impaired by inhibiting the Raf/MEK/ERK pathway with the MEK inhibitor ATR-002 or CI-1040.

The viral infection to be prevented or be treated by the administration of a MEK inhibitor of the invention is an infection caused by a hantavirus. Known hantaviruses include the Puumala virus, the Sin Nombre virus, the Seoul virus, the Hantaan virus, the Dobrava-Belgrad virus, the Saaremaa virus and the Andes virus.

As already mentioned above, hantavirus infections present themselves in two clinical pictures. The first is Hantavirus Hemorrhagic Fever with Renal Syndrome (HFRS), where the mortality rate is 12% and the second is Hantavirus Pulmonary Syndrome (HPS) where the mortality rate is 40%. The severity of the disease depends on the causative hantavirus species and viral load. For example, severe courses of the disease are known to be caused by Hantaan virus, Dobrava-Belgrad virus, Sin Nombre virus and the Andes Virus while more moderate courses of the disease are more likely for example in the Puumala virus or the Saaremaa virus.

Hantavirus hemorrhagic fever with renal syndrome (HFRS) is also known as Korean hemorrhagic fever, epidemic hemorrhagic fever, and nephropathia epidemica. The species that cause HFRS include Hantaan orthohantavirus, Dobrava-Belgrade orthohantavirus, Saaremaa virus, Seoul orthohantavirus, Puumala orthohantavirus and other Eurasian orthohantaviruses. Symptoms of HFRS usually develop within 1 to 2 weeks after exposure to infectious material, but in rare cases, they may take up to 8 weeks to develop. Initial symptoms begin suddenly and include intense headaches, back and abdominal pain, fever, chills, nausea, and blurred vision. Individuals may have flushing of the face, inflammation or redness of the eyes, or a rash. Later symptoms can include low blood pressure, acute shock, vascular leakage, and acute kidney failure, which can cause severe fluid overload.

The severity of the disease varies depending upon the virus causing the infection. Hantaan and Dobrava virus infections usually cause severe symptoms, while Seoul, Saaremaa, and Puumala virus infections are usually more moderate.

This syndrome can also be fatal. In some cases, it has been known to cause permanent renal failure. HFRS is difficult to diagnose on clinical grounds alone and serological evidence is often needed. A fourfold rise in IgG antibody titer in a 1-week interval, and the presence of the IgM type of antibodies against hantaviruses are good evidence for an acute hantavirus infection. HFRS should be suspected in patients with acute febrile flu-like illness, kidney failure of unknown origin and sometimes liver dysfunction.

Hantavirus pulmonary syndrome (HPS) is generally caused by American species of hantavirus. These include Black Creek Canal virus (BCCV), New York orthohantavirus (NYV), Monongahela virus (MGLV), *Sin Nombre orthohantavirus* (SNV), and certain other members of hantavirus genera that are native to the United States and Canada. Specific rodents are the principal hosts of the hantaviruses including the hispid cotton rat (*Sigmodon hispidus*) in southern Florida, which is the principal host of Black Creek Canal virus, the deer mouse (*Peromyscus maniculatus*) in Canada and the Western United States, which is the principal host of Sin Nombre virus and the white-footed mouse (*Peromyscus leucopus*) in the eastern United States, which is the principal host of New York virus. In South America, the *Oligoryzomys longicaudatus* and other species of the genus *Oligoryzomys* have been documented as the reservoir for Andes virus.

Symptoms of HPS are flu-like ones, such as fever, cough, myalgia, headache, lethargy, and shortness of breath, which rapidly deteriorates into acute respiratory failure. It is characterized by the sudden onset of shortness of breath with rapidly evolving pulmonary edema; it is often fatal despite mechanical ventilation and intervention with potent diuretics. It has a fatality rate of 36%. HPS can be easy to overlook because its early symptoms are very similar to the flu. Infected patients suffer from fatigue, fever, and muscle aches often accompanied by headaches, dizziness and gastrointestinal problems in the weeks following exposure. About a week after the initial symptoms subsided, the second phase of the disease sets in, and patients experience severe coughing and shortness of breath as the lungs fill with fluid. In the later stages of HPS, the lungs are severely damaged, resulting in the high fatality rate.

In the use in the treatment or prevention of the invention, the patient preferably is a mammal, in a preferred embodiment a primate, most preferably a human patient. In an alternate administration, treatment of mammals known to be carriers of the hantavirus, such as rodents and bats, specifically, rats, mice and deer mice is contemplated to prevent infection of humans via these hosts. In this context, a broad administration via inhalation (environmental spray formulations) could be considered in areas with high hantavirus infection rates. As transmission human to human is rare in hantavirus infections, such broad application to mammalian non-human hosts, such as rodents, could act as a preventative measure.

In addition, the administration of a MEK inhibitor for prevention of a hantavirus infection to human subjects who have been in contact with rodents or rodent excrements or are living or travelling in a region where a hantavirus outbreak is common could be useful, especially in cases where the human subject has been living or visiting in a region known to have hantavirus infections that result in HFRS or HPS.

Specifically, when the human patient has been travelling or living in Korea, Serbia or in America in areas where a Hantaan or a Dobrava virus infection or a hantavirus infection caused by American species such as Black Creek Canal virus (BCCV), New York orthohantavirus (NYV), Monongahela virus (MGLV), *Sin Nombre orthohantavirus* (SNV), or Andes virus is known, such a preventative or prophylactic treatment would be useful. As transmission of hantavirus species occurs mainly by aerosolized rodent excreta (urine, saliva, feces), preventative treatment could be started immediately after contact with rodent excretions up to 10 days after contact without symptoms of the infection.

The MEK inhibitor may be administered orally, intravenously, intrapleurally, intramuscularly, topically or via inhalation. Preferably, the MEK inhibitor is administered via inhalation or orally.

In addition, the MEK inhibitor may be administered up to 12 hours, up to 24 hours, up to 48 hours, up to 72 hours or between 4 and 10 days after the first symptoms of HFRS or HPS are observed or the human patient has been in contact with rodent excretions.

In one embodiment of the use in the treatment or prevention of the present invention, the compound MEK inhibitor can be administered orally or via inhalation at an effective therapeutic dosage. In one embodiment, the therapeutically effective amount of the MEK inhibitor is, e.g., from 0.1 mg to 2000 mg, 0.1 mg to 1000 mg, 0.1 to 500 mg, 0.1 to 200 mg, 30 to 300 mg, 0.1 to 75 mg, 0.1 to 30 mg.

As outlined above, the present invention further provides a pharmaceutical composition comprising a MEK inhibitor or a pharmaceutically acceptable salt or metabolite thereof for use as a medicament for the prophylaxis and/or treatment of a viral infection, preferably an infection caused by a hantavirus.

The pharmaceutical composition of the invention may be in the form of orally administrable suspensions or tablets; nasal sprays, sterile injectable preparations (intravenously, intrapleurally, intramuscularly), for example, as sterile injectable aqueous or oleaginous suspensions or suppositories. When administered orally as a suspension, these compositions are prepared according to techniques available in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, di-calcium phosphate, starch, magnesium stearate and lactose and/or other excipients, binders, extenders, disintegrants, diluents, and lubricants known in the art. The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. The pharmaceutical compounds in the method of present invention can be administered in any suitable unit dosage forms. Suitable oral formulations also in context of the pharmaceutical composition of the invention can be in the form of tablets, capsules, suspension, syrup, chewing gum, wafer, elixir, and the like. Pharmaceutically acceptable carriers such as binders, excipients, lubricants, and sweetening or flavoring agents can be included in the oral pharmaceutical compositions. If desired, conventional agents for modifying tastes, colors, and shapes of the special forms can also be included.

For injectable formulations, the pharmaceutical compositions can be in lyophilized powder in admixture with suitable excipients in a suitable vial or tube. Before use in the clinic, the drugs may be reconstituted by dissolving the lyophilized powder in a suitable solvent system to form a composition suitable for intravenous or intramuscular injection.

In one embodiment, the pharmaceutical composition can be in an orally administrable form (e.g., tablet or capsule or syrup etc.) with a therapeutically effective amount (e.g., from 0.1 mg to 2000 mg, 0.1 mg to 1000 mg, 0.1 to 500 mg, 0.1 to 200 mg, 30 to 300 mg, 0.1 to 75 mg, 0.1 to 30 mg) of MEK inhibitor.

Definitions

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

EXAMPLES

Materials

Puumala virus (PUUV) Strain Sotkamo
Main hantavirus species in Europe
Can be handled in a S2 laboratory
Vero cell line
Cell line derived from African green monkey kidney cells
Routinely used for growing viruses
Type I interferon deficient
Cell culture media:
Base Medium: IMDM, 1% P/S, 1% L-Gln, 10% FCS
ATR-002/CI-1040 treatment medium: Base medium w/o FCS
Virusinfection medium: Base medium w/o FCS The MEK inhibitor ATR-002 (PD0184264) [2-(2-chloro-4-iodophenylamino)-N-3,4-difluoro benzoic acid, the active metabolite of CI-1040, was synthesized at ChemCon GmbH (Freiburg, Germany).

The MEK inhibitor CI-1040 [2-(2-chloro-4-iodophenylamino)-N-(cyclopropylmethoxy)-3,4-difluorobenzamide] was synthesized at ChemCon GmbH (Freiburg, Germany).

Example 1: Virus Yield Reduction Assay

Methods

Vero cells were seeded in 24-well plates ($1\times10^6$ cells/well), incubation at 37° C., 5% $CO_2$.

One day post seeding the cells were infected with PUU-Virus particles (MOI 0.3).

1 h post infection the cells were treated with either 40 μM CI-1040, 40 μM ATR-002 or DMSO (solvent control).

The supernatants were collected 72 h post infection and the virus titer was determined via $TCID_{50}$ assay below.

$TCID_{50}$ Assay (SOP-ATR-0119)

Virus titration was performed using the standard operating procedure SOP-ATR-0119. Briefly, 10% homogenates from lungs and kidneys/supernatants from the VYR assay were diluted in a 1:10 serial dilution. Vero cells were infected with the different 10-fold virus dilutions and incubated for 60 min at 37° C. in a 5% $CO_2$ atmosphere. After incubation, cells were rinsed with PBS and supplemented with 200 μl IMDM (Iscove's Modified Dulbecco's Medium)/BA (Bovine Albumin)–Medium (0.2% BA, 1 mM $MgCl_2$, 0.9 mM $CaCl_2$, 100 U/ml penicillin, 0.1 mg/ml streptomycin) and incubated for 7 days at 37° C. in 5% $CO_2$. Thereafter Vero cells were washed and fixed with Roti®-Histofix for 30 min at 4° C. After washing with PBS, the cells were permeabilized with Triton-X-100 and FCS. The incubation of the primary antibody (Anti-PUUV-NP-AB) was hold for one hour. After washing, the secondary antibody was given to the cells for 30 min. Afterwards, the cells were washed and stained with the substrate TrueBlue for 10 min. The analysis was done by light microscopy.

Results

Figure 1:
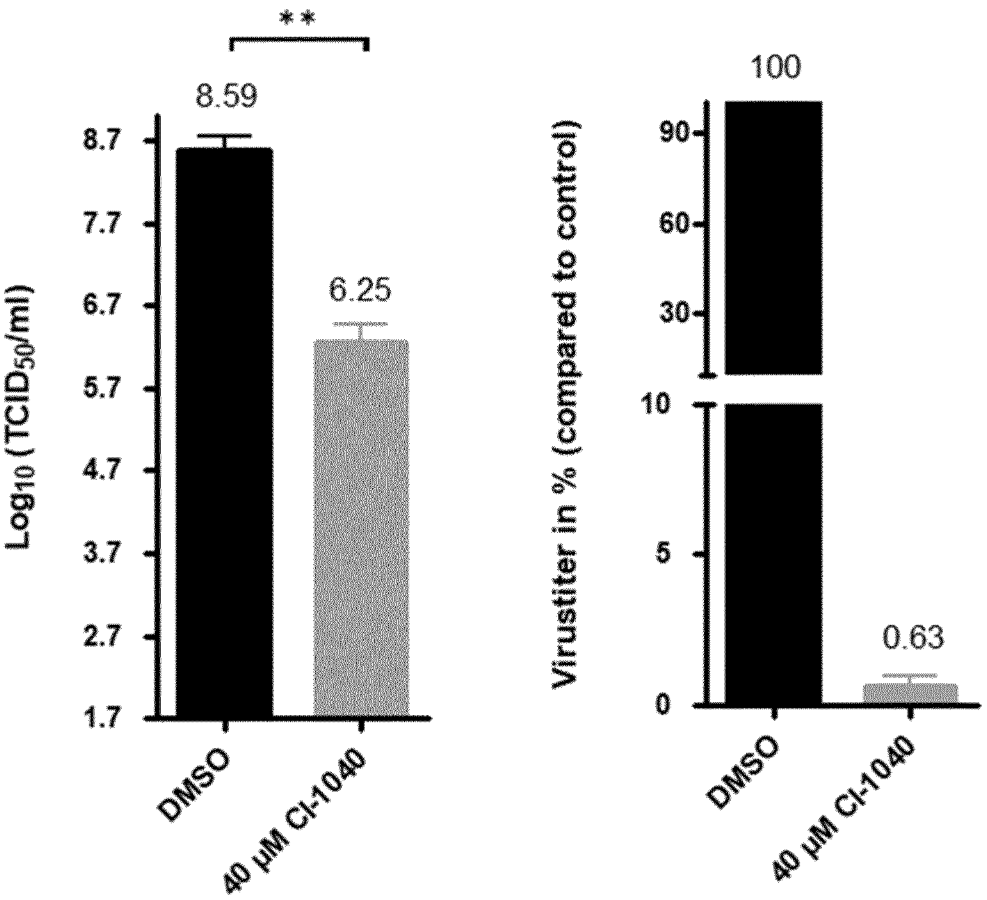
FIG. 1 shows that in presence of CI-1040, a significant virus titer reduction of >2 $\log_{10}$-steps was achieved compared to the solvent control. This equals a virus titer reduction of >99%.

As can be seen from FIG. 1, in presence of CI-1040, a significant virus titer reduction of >2 $\log_{10}$-steps was achieved compared to the solvent control. This equals a virus titer reduction of >99%.

Figure 2:
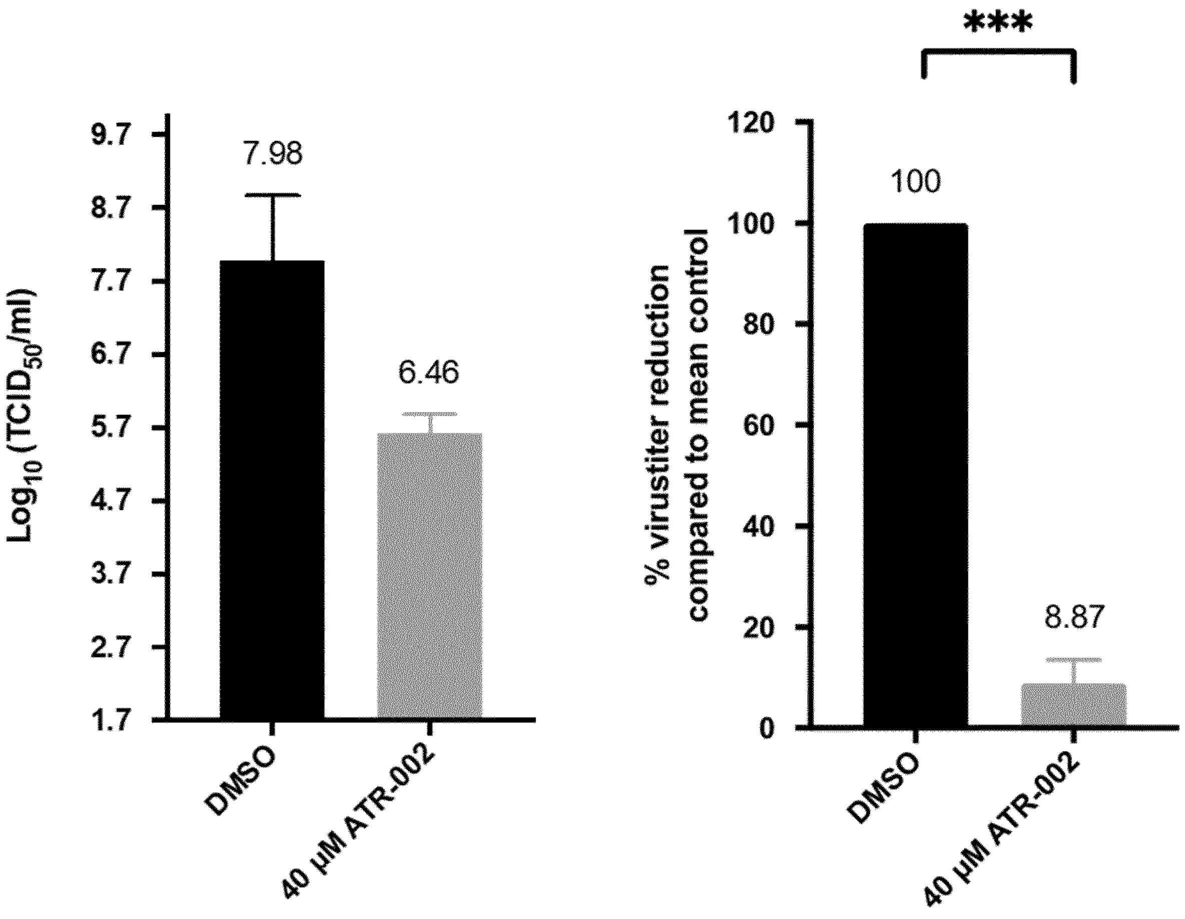
FIG. 2 shows that in presence of ATR-002, a virus titer reduction of >1.5 $\log_{10}$-steps was achieved compared to the solvent control. This equals a virus titer reduction of >90%.

Similar results are seen in FIG. 2, in presence of ATR-002, where a virus titer reduction of >1.5 $\log_{10}$-steps was achieved compared to the solvent control. This equals a virus titer reduction of >90%.

Conclusion

Treatment of Vero cells infected with PUUV (MOI 0.3) with either 40 μM CI-1040 or 40 μM ATR-002 lead to a strong virus titer reduction compared to a solvent control.

Inhibition of the Raf/MEK/ERK-pathway impaired the propagation of the Puumala virus in vitro.

Example 2: Antiviral Effect Of Air-002 Against Hantavirus In Vivo

Material and Methods

Mice

No robust established animal model to study Hantavirus infections was available. The type I interferon deficient Vero cells proved to be a good in vitro model, but no type I interferon deficient mice were available. Therefore, interferon receptor knock-out mice (IFNα/β/γR−/− (AG129) mice) were chosen for the in vivo studies. AG129 mice were used in the following Experiments.

Methods

AG129 mice were infected with PUUV intranasally ($5\times10^5$/pfu in 50 μl PBS, inoculation with 25 μl into each nostril).

Treatment with 75 mg/Kg/Day of ATR-002 (in DMSO/Cremophor EU PBS), beginning 5 h post infection for 5 consecutive days. Administration route: oral by gavage, 37.5 mg/kg twice daily (9 am and 6 pm). Treatment of the control group with solvent only accordingly.

The mice were sacrificed on day 7 and day 10 post infection to determine the virus titer in lung and kidneys ($TCID_{50}$ Assay).

Results

None of the animals lost weight, developed clinical symptoms or died after PUUV infection.

PUUV was detectable in the solvent control animals in the lung and in the kidney at day 7 and day 10 post infection. The virus titer was higher on day 10.

In the lung and the kidney of the treated animals with 75 mg/kg/Day ATR-002 no virus could be detected at day 7 and 10 post infection (limit of detection: Lung: 3.4 $\log_{10}$ ($TCID_{50}$/g organ) Kidney: 3.2 $\log_{10}$($TCID_{50}$/g organ)) as can be seen in FIGS. 3 and 4, respectively.

The reduction in the amount of virus (comparison between the homogenates treated with solvent control and treated with ATR-002) were highly significant (2-way-ANOVA, $P<0.0001$).

Conclusion

The study demonstrated that five days treatment of mice with 75 mg/Kg/Day of ATR-002 (in DMSO/Cremophor EUPBS), starting 5 hours post PUUV infection, significantly reduced the amount of virus in the lung and the kidneys.

The invention claimed is:

1. A method of preventing or treating of a hantavirus infection in a mammal comprising:

identifying the mammal as in need of prophylaxis on the basis of exposure to hantavirus infection or as in need of treatment on the basis of evidence of an acute hantavirus infection, administering to the mammal in need thereof a therapeutically effective amount of a MEK inhibitor, wherein the MEK inhibitor is CI-1040 or PD-0184264, or pharmaceutically acceptable salt or metabolite thereof.

2. The method of claim 1, wherein the mammal is a rodent or a human.

3. The method of claim 2, wherein the mammal is a human and the human shows symptoms of Hantavirus Hemorrhagic Fever with Renal Syndrome (HFRS), or Hantavirus Pulmonary Syndrome (HPS).

4. The method of claim 3, wherein the MEK inhibitor is administered up to 12 hours, up to 24 hours, up to 48 hours, up to 72 hours or between 4 and 10 days after the first symptoms of HFRS or HPS are observed.

5. The method of claim 1, wherein the mammal is a human identified as having an exposure to rodents or rodent excrement within a period of between 12 hours and 10 days prior to the administration, and wherein the MEK inhibitor is administered for prevention of hantavirus infection.

6. The method of claim 2, wherein the human subject has been living or visiting in a region known to have hantavirus infections that result in HFRS or HPS.

7. The method of claim 6, wherein the hantavirus is a Hantaan or a Dobrava virus infection or a hantavirus infection caused by a Hantavirus species selected from the group consisting of Black Creek Canal virus (BCCV), New York orthohantavirus (NYV), Monongahela virus (MGLV), Sin Nombre orthohantavirus (SNV), and Andes virus.

8. The method of claim 1, wherein the MEK inhibitor is administered orally or via inhalation.

9. The method of claim 2, wherein the mammal is a rodent and the MEK inhibitor is administered to rodent populations to prevent infection of humans in contact with the rodents.

10. The method of claim 9, wherein the MEK inhibitor is administered by inhalation.

11. A method of preventing a hantavirus infection in a mammal comprising:

identifying the mammal as in need of prophylaxis on the basis of having an exposure to rodents or rodent excrement within a period of between 12 hours and 10 days prior to the administration, administering to the mammal in need thereof a therapeutically effective amount of a MEK inhibitor, wherein the MEK inhibitor is CI-1040 or PD-0184264, or pharmaceutically acceptable salt or metabolite thereof.

12. The method of claim 11, wherein the mammal is a rodent or a human.

13. The method of claim 12, wherein the MEK inhibitor is administered orally or via inhalation.

14. The method of claim 13, wherein the MEK inhibitor is administered by inhalation.

* * * * *